US00PP29300P3

(12) United States Plant Patent
Park et al.

(10) Patent No.: US PP29,300 P3
(45) Date of Patent: May 22, 2018

(54) ***CITRUS RETICULATA* BLANCO PLANT NAMED 'TAMDO NO.3'**

(50) Latin Name: ***Citrus reticulata* Blanco**
Varietal Denomination: Tamdo No.3

(71) Applicant: THE RURAL DEVELOPMENT ADMINISTRATION, REPUBLIC OF KOREA, Chungcheongnam-Do (KR)

(72) Inventors: Jaeho Park, Seogwipo-si (KR); Su-Hyun Yun, Jeollabuk-Do (KR); Sangwoog Koh, Jeollabuk-Do (KR); Minju Kim, Seogwipo-si (KR); Yonghun Choi, Seogwipo-si (KR); Donghoon Lee, Jeollabuk-Do (KR); I-Ung Yang, Seogwipo-si (KR); Chiwon Chae, Seogwipo-si (KR)

(73) Assignee: The Rural Development Administration, Republic of Korea, Seonghwan-Eup Seobug-gu Cheonan-Si Chungcheongnam-Do ( * ) Notice: Subject to any disclaimer, the term of this patent is extended or adjusted under 35 U.S.C. 154(b) by 0 days. days.

(21) Appl. No.: 14/998,683

(22) Filed: Feb. 2, 2016

(65) Prior Publication Data

US 2017/0223884 P1 Aug. 3, 2017

(51) Int. Cl.
*A01H 5/08* (2018.01)

(52) U.S. Cl.
USPC ..... Plt./202

(58) Field of Classification Search
USPC ..... Plt./202
See application file for complete search history.

(56) References Cited

PUBLICATIONS

Korea Seed & Variety Service Applications, Appl. No. 2013-353, Aug. 15, 2013.

*Primary Examiner* — Keith O Robinson
(74) *Attorney, Agent, or Firm* — Baker, Donelson, Bearman, Caldwell & Berkowitz, PC

(57) ABSTRACT

A new and distinct *Citrus Reticulate* Blanco plant named 'Tamdo No. 3', characterized by its upright plant type and strong vigor, The plant type of 'Tamdo No.3' is upright and the tree vigor is strong, fruit shape is oblate and the fruit shape index is about 143, fruit skin thickness is about 2.7 mm so it is easy skinning, the fruit flesh rate is about 82.9%, sugar of fruit juice is about 13.7° Bx, the acidity is about 0.79%, and the sugar acid ratio is about 17.34.

2 Drawing Sheets

Latin name of the genus and species of the plant claimed: *Citrus reticulata* Blanco.

Variety denomination: 'Tamdo No.3'.

BACKGROUND OF THE INVENTION

The new and distinct cultivar is a product of a breeding program conducted in a nursery in Korea and by the inventors by crossing a Japanese variety 'Kiyomi' (not patented, as the seed parent) and an American variety 'Sunburst' mandarin (not patented, as the pollen parent). The seeds obtained by the cross were sowed in the next spring. The plants started fruiting in 2010. In 2011, the first screening was carried out, and the one called Jegamna-27 was selected. In the last screening which was carried out in 2012, Jegamna-27 was selected as a new variety and named 'Tamdo No.3'.

After hybridization of the parents, the variety was planted by asexual propagation by grafting in Korea for three generations and there was no genetic variation, therefore its traits are stable.

The fruit characteristics of 'Tamdo No.3' are in the Table 1 below. The test carried out from 2010 to 2012, in *Citrus* Research Station.

| Survey date (yyyy.mm.dd) | Fruit weight (g) | Flesh rate (%) | Fruit shape index | Thickness of the skin (mm) |
|---|---|---|---|---|
| 2010.1.6 | 254.2 | 85.9 | 155 | 1.7 |
| 2010.3.22 | 173.9 | 77.9 | | 3.0 |
| 2011.1.5 | 189.8 | 85.1 | 157 | 1.5 |
| 2011.1.20 | 213.8 | 82.3 | 155 | 2.1 |
| 2011.2.7 | 200.8 | 81.9 | 149 | 2.7 |
| 2011.2.21 | 171.6 | 82.7 | 152 | 2.3 |
| 2011.3.8 | 232.6 | 78.5 | 152 | 2.8 |
| 2011.3.29 | 262.2 | 81.4 | 158 | 2.4 |
| 2012.2.6 | 290.8 | 84.6 | 149 | 2.3 |
| 2012.2.20 | 280.0 | 82.9 | 143 | 2.7 |
| 2012.3.13 | 284.6 | 82.6 | 141 | 2.2 |

| Survey date (yyyy.mm.dd) | Seed grain number | Sugar (° Bx) | Acidity (%) | Sugar acid ratio |
|---|---|---|---|---|
| 2010.1.6 | 0.0 | 10.8 | 0.82 | 13.19 |
| 2010.3.22 | 2.4 | 11.8 | 1.22 | 9.66 |
| 2011.1.5 | 0.6 | 12.9 | 1.28 | 10.13 |
| 2011.1.20 | 0.0 | 12.7 | 1.28 | 10.46 |
| 2011.2.7 | 0.0 | 14.0 | 1.09 | 13.02 |
| 2011.2.21 | 0.0 | 14.4 | 1.31 | 11.20 |
| 2011.3.8 | 0.0 | 14.7 | 1.06 | 13.85 |
| 2011.3.29 | 0.0 | 13.5 | 0.85 | 16.05 |

-continued

| | | | | |
|---|---|---|---|---|
| 2012.2.6 | 0.0 | 12.9 | 0.88 | 14.69 |
| 2012.2.20 | 0.0 | 13.7 | 0.79 | 17.34 |
| 2012.3.13 | 0.0 | 13.8 | 0.82 | 16.77 |

Fruit shape index = The transverse diameter ÷ The longitudinal diameter × 100

SUMMARY OF THE INVENTION

The cultivar 'Tamdo No. 3' has not been observed under every possible environmental conditions. Therefore, there may be variations in the phenotype due to varying environmental conditions such as temperature, day length and light intensity. However, the genotype will not vary.

The following traits have been repeatedly observed and are determined to be the characteristics of the new cultivar of *Citrus reticulata* Blanco. These attributes in combination distinguish 'Tamdo No. 3' as unique from all other varieties of *Citrus reticulata* Blanco known to the inventors.

1. The plant type of 'Tamdo No.3' is upright and the tree vigor is strong.
2. The fruit color is orange.
3. Germination stage of 'Tamdo No.3' is in the middle of April, and the blooming stage is in late May.
4. Fruits start coloring in late October and finish coloring in early December.
5. The mature stage is in the middle of February.
6. Fruit shape is oblate and the fruit shape index is about 143.
7. Fruit skin thickness is about 2.7 mm so it is easy skinning.
8. The fruit flesh rate is about 82.9%.
9. Sugar of fruit juice is about 13.7° Bx, the acidity is about 0.79%, and the sugar acid ratio is about 17.34.

Plants of the new cultivar 'Tamdo No. 3' are similar to plants of the seed parent 'Kiyomi' in most horticultural characteristics, however, the plants of the new cultivar 'Tamdo No. 3' produce tree vigor that are stronger than the parent. Compared to the parent, 'Tamdo No. 3' produces fruit with skin thickness of about 2.7 mm. The fruit surface of the new cultivar is smooth, whereas the 'Kiyomi' cultivar has a rough fruit surface.

The new cultivar differs from the closest comparable plants and characteristics of the new cultivar as shown in the tables below:

TABLE 2

| Denomination of similar variety | Characteristic in which the similar variety is different | The expression of the characteristic: Kiyomi Variety | Tamdo No. 3 Variety |
|---|---|---|---|
| Kiyomi | plant: type | medium | upright |
| | Tree vigor | medium | strong |
| | Fruit: shape index | 119 (round) | 143 (oblate) |
| | Fruit: flesh rate | 74.6% | 82.9% |
| | Fruit: skin thickness | 4.9 mm | 2.7 mm |
| | Fruit: skin surface | rough | smooth |
| | Fruit juice: Sugar (° Bx) | 9.7 | 13.7 |
| | Fruit juice: Acidity (%) | 1.17 | 0.79 |
| | Fruit: sugar acid ratio | 8.29 | 17.34 |
| | Fruit: color | yellowish orange | medium orange |

TABLE 2-continued

| Denomination of similar variety | Characteristic in which the similar variety is different | The expression of the characteristic: Kiyomi Variety | Tamdo No. 3 Variety |
|---|---|---|---|
| | Mature stage | early (in the middle of March) | very early (in the middle of February) |

TABLE 3

| Variety | Fruit weight (g) | Flesh rate (%) | Fruit shape index | Thickness of the skin (mm) | Seed grain number |
|---|---|---|---|---|---|
| Tamdo No.3 | 213.8 | 82.3 | 155 | 2.1 | 0.0 |
| Kiyomi | 214.0 | 74.4 | 107 | 4.1 | 0.0 |
| T-Test (0.05) | NS | * | * | * | |
| Tamdo No.3 | 232.6 | 78.5 | 152 | 2.8 | 0.0 |
| Kiyomi | 209.9 | 70.5 | 118 | 4.8 | 0.0 |
| T-Test (0.05) | NS | * | * | * | |
| Tamdo No.3 | 280.0 | 82.9 | 143 | 2.7 | 0.0 |
| Kiyomi | 318.7 | 74.6 | 119 | 4.9 | 0.0 |
| T-Test (0.05) | NS | * | * | * | |

| Variety | Sugar (° Bx) | Acidity (%) | Sugar acid ratio | Degree of color (a*) | Survey date (yyyy.mm.dd) |
|---|---|---|---|---|---|
| Tamdo No.3 | 12.7 | 1.28 | 10.46 | 30.8 | 2011.1.20 |
| Kiyomi | 10.1 | 1.75 | 5.99 | 18.7 | 2011.1.20 |
| T-Test (0.05) | * | NS | * | * | |
| Tamdo No.3 | 14.7 | 1.06 | 13.85 | 33.6 | 2011.3.8 |
| Kiyomi | 10.3 | 1.55 | 6.68 | 22.6 | 2011.3.9 |
| T-Test (0.05) | * | * | * | * | |
| Tamdo No.3 | 13.7 | 0.79 | 17.34 | 31.1 | 2012.2.20 |
| Kiyomi | 9.7 | 1.17 | 8.29 | 18.7 | 2012.2.20 |
| T-Test (0.05) | * | * | * | * | |

TABLE 4

| NO | Characteristics | Forms of Expression 1 | 2 | 3 | 4 | 5 |
|---|---|---|---|---|---|---|
| 1 | Chromosome multiple | | 2 | 3 | 4 | |
| 2 | Plant: Type | upright | | | | medium |
| 3 | Plant: density of spines | no or sparse | | | | medium |
| 4 | leaf: color | light green | | | | green |
| 5 | leaf: length | very short | | short | | medium |
| 6 | leaf: width | very narrow | | narrow | | medium |

TABLE 4-continued

| | | | | | | |
|---|---|---|---|---|---|---|
| 7 | leaf: length/ width ratio | small | | | | medium |
| 8 | Leaf petiole: length | very short | | short | | medium |
| 9 | Flower: calyx diameter | small | | | | medium |
| 10 | Flower: petal length | very short | | short | | medium |
| 11 | Flower: petal width | very narrow | | narrow | | medium |
| 12 | Flower: petal length/ width ratio | small | | | | medium |
| 13 | Flower: stamen length | very short | | short | | medium |
| 14 | Flower: anther color | white NN155A | | | | light yellow |
| 15 | Flower: activity pollen | absent | | | | |
| 16 | Fruit: length | very short | | short | | medium |
| 17 | Fruit: width | very narrow | | nanow | | medium |
| 18 | Fruit: length/width ratio | small | | | | medium |
| 19 | Fruit: neck | absent | | | | |
| 20 | Fruit: areola | absent | | | | |
| 21 | Fruit: surface color | green | yellowish green | light yellow | medium yellow | yellowish orange (26B) |
| 22 | Fruit: surface roughness | smooth | | | | |
| 23 | Fruit: fresh color | with white | light green | light yellow | medium yellow | light orange (24A) |
| 24 | Fruit: skin thickness | thin | | | | medium |
| 25 | Fruit: skin strength | weak | | | | medium |
| 26 | Fruit juice: total soluble solids | low | | | | medium |
| 27 | Fruit juice: acid | low | | | | medium |
| 28 | Mature stage | very early | | early | | medium |
| 29 | Partheno-carpy | absent | | | | |
| 30 | Self-incompat-ibility | absent | | | | |
| 31 | Tree vigor | weak | | | | medium |

| | Forms of Expression | | | | Application variety: Tamdo No. 3 | | Similar variety: Kiyomi | |
|---|---|---|---|---|---|---|---|---|
| NO | 6 | 7 | 8 | 9 | No | Data | No | Data |
| 1 | | | | | 2 | | 2 | |
| 2 | | | | pen-dulous | 1 | | 5 | |
| 3 | | | | densely | 1 | | 1 | |
| 4 | | | | dark green (137A) | 9 | | 9 | |
| 5 | | long | | very long | 5 | 10.3 cm | 7 | 12.7 cm |
| 6 | | broad | | very broad | 5 | 4.8 cm | 7 | 5.8 cm |
| 7 | | | | large | 5 | 2.2 | 5 | 2.2 |
| 8 | | long | | very long | 3 | 14.9 mm | 5 | 21.7 mm |
| 9 | | | | large | 5 | | 5 | |
| 10 | | long | | very long | 5 | 18.2 mm | 5 | 16.1 mm |
| 11 | | broad | | very broad | 5 | 8.9 mm | 5 | 7.7 mm |
| 12 | | | | large | 5 | 2.0 | 5 | 2.1 |
| 13 | | long | | very long | 5 | | 5 | |
| 14 | | | | medium yellow | 1 | | 1 | |
| 15 | | | | present | 1 | | 1 | |
| 16 | | long | | very long | 5 | 59.7 mm | 7 | 73.5 mm |
| 17 | | large | | very large | 7 | 89.4 mm | 7 | 84.3 mm |
| 18 | | | | large | 5 | 0.67 | 9 | 0.87 |
| 19 | | | | present | 9 | | 1 | |
| 20 | | | | present | 1 | | 1 | |
| 21 | medium orange (30D) | dark orange | red with orange | red | 6 | 31.8(a) | 5 | 20.0(a) |
| 22 | | | | rough | 1 | | 9 | |
| 23 | medium orange (25A) | dark orang | red | purple | 6 | | 4 | |
| 24 | | | | thick | 5 | 2.7 mm | 9 | 4.9 mm |
| 25 | | | | strong | 5 | | 9 | |
| 26 | | | | high | 9 | 13.7° Bx | 5 | 9.7° Bx |
| 27 | | | | high | 1 | | 5 | |
| 28 | | late | | very late | 1 | | 3 | |
| 29 | | | | present | 9 | | 9 | |
| 30 | | | | present | 9 | | 9 | |
| 31 | | | | strong | 9 | | 5 | |

Table 5 illustrates the comparison of the claimed plant with that of the pollen parent 'Sunburst' and a related know variety 'Kanpei'.

TABLE 5

| Characteristic(s) in which the candidate variety differs from the similar variety(ies) | Describe the expression of the characteristic(s) for the candidate variety 'Tamdo No. 3' | Describe the expression of the characteristic(s) for the similar variety 'Sunburst' | Describe the expression of the characteristic(s) for the similar variety 'kanpei' |
|---|---|---|---|
| Plant: Type | upright | upright | spreading |
| Flower: activity pollen | absent | present | absent |
| Fruit: width | 89.4 mm | 66.5 mm | 73.0 mm |
| Fruit: neck | present | absent | absent |
| Fruit: presence of navel | absent or very rare | always present | absent or very rare |
| Fruit juice: total soluble solids | 13.7° Bx | 11.4° Bx | 11.1° Bx |
| Fruit juice: acid | 0.79% | 0.84% | 1.11% |
| Fruit: number of seeds | 0 | 10 | 0 |
| Mature stage | Mid-late(mid-February) | Early(Mid-november) | Middle(mid-January) |
| Parthenocarpy | presen | absent | present |
| Self-incompatibility | present | present | present |
| Tree vigor | strong | strong | middle |

BRIEF DESCRIPTION OF THE DRAWINGS

The accompanying colored photographs illustrate the overall appearance and distinct characteristics of the new *Citrus reticulate* Blanco 'Tamdo No. 3' showing colors as true as is reasonably possible with colored reproduction of this type. The age of the plant in the photos are approximately 9 years. These photos were taken in 2012, in Korea. Colors in the photographs may differ slightly from the color values cited in the detained botanical description which accurately describes the color of the 'Tamdo No. 3'.

The chart used in the identification of colors described herein is The R.H.S. Colour Chart of The Royal Horticultural Society, 2007, Fifth edition, except where general color terms of ordinary significance are used.

DETAILED BOTANICAL DESCRIPTION

Figure 1:
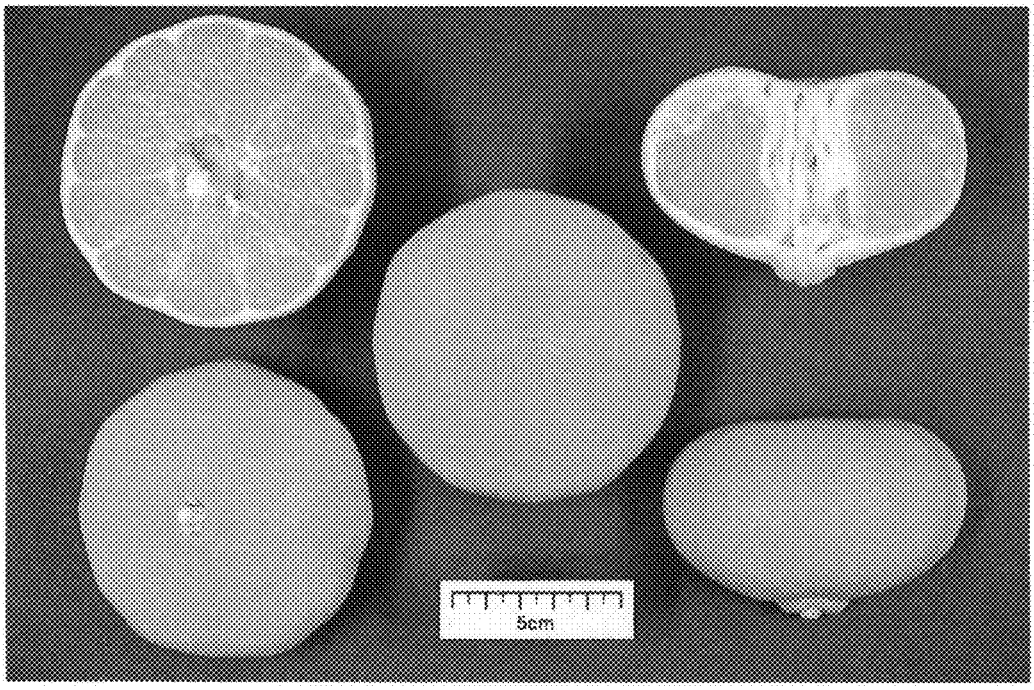
FIG. 1 provides multiple views of typical fruits harvested from the cultivar 'Tamdo No. 3'. Top, bottom and side views of the whole, unpeeled fruit are shown as well as two cross-sectional views of the inside of the fruit.
Figure 2:
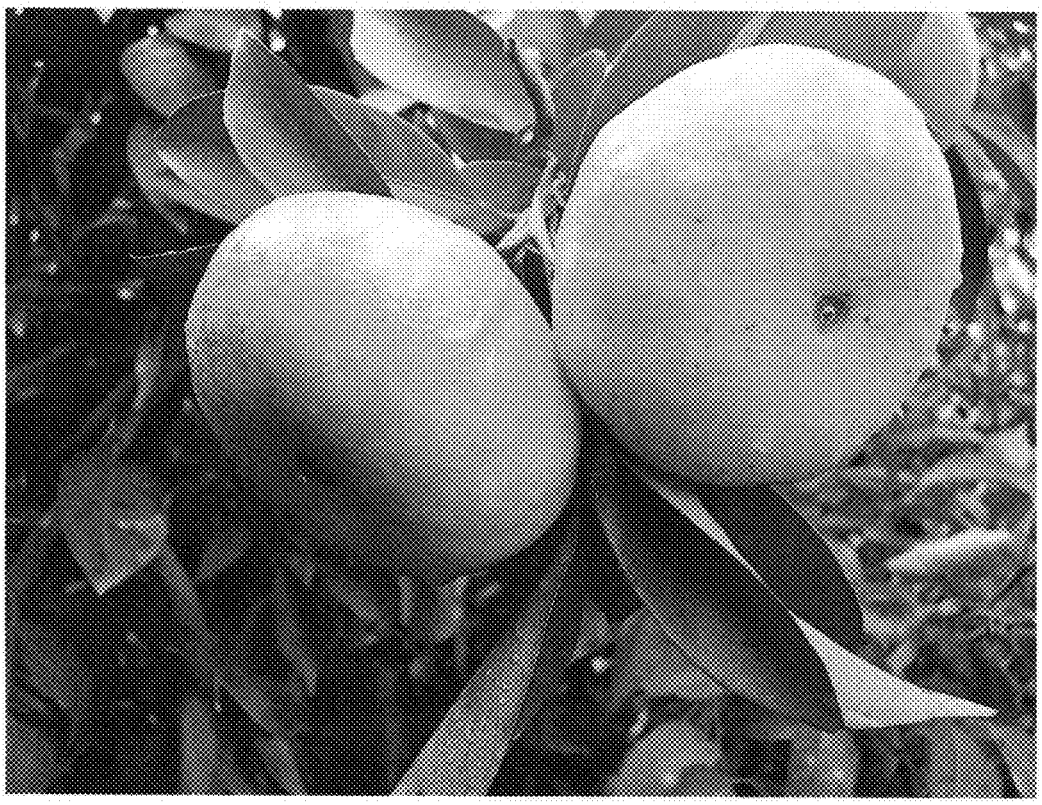
FIG. 2 illustrates in full color typical foliage and fruits of 'Tamdo No. 3' on the tree.

The following is a detailed description of the new cultivar 'Tamdo No. 3' plants as grown in Korea. The descriptions were taken from 2010 to 2012.

Botanical classification: *Citrus reticulate* Blanco 'Tamdo No. 3'.

Propagation: 'Tamdo No. 3' is typically grafted onto rootstock of 'Jegamna-27'.

Plant:

*Age of the plant described*.—Approximately 3 years.
*Chromosome multiples*.—2.
*Plant type*.—Upright.
*Plant tree vigor*.—Strong.
*Plant density of spines*.—None or sparse.

Foliage:

*Leaf color*.—Dark green (R.H.S. Green 137A).
*Leaf length*.—About 10.3 cm.
*Leaf width*.—About 4.8 cm.
*Leaf length/width ratio*.—About 2.2.
*Leaf petiole length*.—About 14.9 mm.
*Leaf shape*.—Ovate.
*Margin of leaf*.—Absent or weak.
*Apex of leaf*.—Acute.

Flower:

*Flower calyx diameter*.—About 3.2 mm.
*Flower petal length*.—About 18.2 mm.
*Flower petal width*.—About 8.9 mm.
*Flower petal length/width ratio*.—About 2.0.
*Flower stamen length*.—About 7.7 mm.
*Flower anther color*.—White (R.H.S. White NN155A).
*Flower activity pollen*.—Absent.

Fruit:

*Fruit length*.—About 59.7 mm.
*Fruit width*.—About 89.4 mm.
*Fruit length/width ratio*.—About 0.67.
*Fruit neck*.—Present.
*Fruit areola*.—Absent.
*Fruit surface color*.—Medium orange (R.H.S. Orange 30D).
*Fruit surface roughness*.—Smooth.
*Fruit fresh color*.—Medium orange (R.H.S. Orange 25A).
*Fruit skin thickness*.—About 2.7 mm.
*Fruit skin strength*.—Medium.
*Fruit flesh rate*.—About 82.9%.
*Fruit sugar acid ratio*.—About 17.34.
*Fruit juice*.—Total soluble solids: about 13.7° Bx.
*Fruit juice acidity*.—About 0.79%.
*Mature stage*.—Very early.
*Parthenocarpy*.—Present.
*Self-incompatibility*.—Present.
*Tree vigor*.—Strong.
*Position of the broadest part of the fruit*.—At middle.
*Shape of the fruit*.—Oblate.
*Width of the fruit neck*.—About 16.2 mm.
*Length of the fruit neck*.—About 6.5 mm.
*The presence of depression at distal end of the fruit*.—Absent.
*The glossiness of the fruit surface*.—Moderate.
*The adherence to the flesh of the fruit rind*.—Weak.
*The presence of the navel of fruit*.—Absent.
*The time of maturity of fruit for consumption*.—Mid-late (mid-February).
*The polyembryony of the seed*.—Absent.
*Seed*.—Absent.
*Other fruit features*.—For the very early mature stage, 'Tamdo No.3' should be protected cultured. Pruning on 'Tamdo No.3' is as the same as other variety which belongs to *Citrus reticulata* Blanco.

What is claimed is:

1. A new and distinct cultivar of *Citrus reticulate* Blanco plant named 'Tamdo No. 3' as herein illustrated and described.

* * * * *